United States Patent [19]

Seibel

[11] Patent Number: 4,916,132
[45] Date of Patent: Apr. 10, 1990

[54] USE OF DIHYDROERGOTAMINE AND ITS SALTS FOR THE LOCAL TREATMENT OF TROPHIC DISTURBANCES

[75] Inventor: Hubert Seibel, Aachen, Fed. Rep. of Germany

[73] Assignee: Dr. Rentschler Arzneimittel GmbH & Co., Laupheim, Fed. Rep. of Germany

[21] Appl. No.: 171,545

[22] Filed: Mar. 22, 1988

[30] Foreign Application Priority Data

Mar. 27, 1987 [DE] Fed. Rep. of Germany ....... 3710216

[51] Int. Cl.[4] .................... A61K 31/50; A61K 31/495
[52] U.S. Cl. .................................... 514/250; 514/928
[58] Field of Search ................................ 514/250, 928

[56] References Cited
U.S. PATENT DOCUMENTS
4,758,423  7/1988  Azria et al. .......................... 514/250

OTHER PUBLICATIONS
Chemical Abstracts, 96:91641f, (Nauarro et al.), 1982.
Chemical Abstracts, 100:39654z, (Stroetmann), 1984.

Primary Examiner—Leonard Schenkman
Attorney, Agent, or Firm—Gordon W. Hueschen

[57] ABSTRACT

The present invention relates to the use of dihydroergotamine and its salts for the local treatment of trophic disturbances, to drug forms for the local application of dihydroergotamine for the treatment of trophic disturbances and to methods for the production thereof, the concentrations of active substance in the drug compositions being between 0.001 and 99.9% by weight.

18 Claims, No Drawings

USE OF DIHYDROERGOTAMINE AND ITS SALTS FOR THE LOCAL TREATMENT OF TROPHIC DISTURBANCES

FIELD AND BACKGROUND OF INVENTION

The present invention relates to the use of dihydroergotamine and its salts for the local treatment of trophic disturbances which manifest themselves clinically in the form of stasis dermatoses, ulcers and tissue death. The invention also concerns drug dosage forms for local application which contain dihydroergotamine and/or its salts and are suitable for the treatment of trophic disturbances, as well as methods for the production thereof.

Trophic disturbances are nutrition-induced, and thus growth-induced, disturbances in the nutrition of the tissue or of organs, stasis dermatoses and ulcers of the veins of the lower leg (ulcus cruris venosum) being the most severe consequences of chronic venous insufficiency, caused by a constitutional, protonic weakening of the vein walls or the consequence of thrombotic diseases.

Another form of trophically-produced disturbances of the skin are decutibal ulcers, caused by regional disturbances in the circulation of immobilized bed-ridden patients.

From epidemiological studies it has been found that about 2% of the population of the industrial countries have ulcers in the region of their legs, about 90% thereof being caused by veins (Schmidle et al., Pharmakritic 8, 6, 1986, pages 21-24). It is clear from this that, in addition to the limited quality of life of the persons affected, considerable economic losses also result, due to stays in hospital and inability to work. Up to now there has been no clear standard medicinal treatment for ulcus cruris venosum, stasis dermatoses and decubital ulcers. Rather, these diseases are treated polypragmatically by symptomatic treatment, with results which in the final analysis are uncertain. In accordance with traditional medicine the treatment comprises cleaning the ulcer by mechanical, osmotic, or enzymatic methods, simultaneous antimicrobial or antiphlogistic treatment and the use of granulation-promoting and epithelizing agents (M. Mörl, Fortschr. Med. 104, 1986, No. 21), generally with the application of pressure bandages in order to obtain venous flow physically, and lack of movement. The doubtful nature of these methods of treatment is described by Schmidli and Holzer in an article entitled "Lokale Behandlung von Hautulcera" [Local Treatment of Ulcers of the Skin] published in Pharmakritic 8, 6, 1986.

The use of dihydroergotamine and its salts in medicinal forms for peroral and parenteral application for promoting vasotonia in order to treat hypotonic orthostatic dysregulation (low blood pressure), attacks of migraine and chronic venous insufficiency as well as assure migraine prophylaxis is known.

The local application of dihydroergotamine for the treatment of trophic disturbances such as, for instance, stasis dermatosis, ulcus cruris venosum, and decubital ulcers has not been known up to the present time.

It has surprisingly been discovered that said diseases can be successfully treated if—contrary to the classical use of dihydroergotamine and its salts—they are applied locally. It was furthermore surprisingly found that wet and discharging open wounds in the case of ulcerations dry up after only a short time under the action even of liquid forms of administration. It is possible in such case to dispense completely with the use of antibiotics and cleansing agents for the control of the bacterial infections which customarily occur and make the treatment even more difficult. It was furthermore surprising that, after only a short period of time as compared with the customary time of treatment, vascularization from the depth of the ulcer could be observed as well as clearly visible granulation islands.

Furthermore, it was surprisingly found that the healing takes place both from the depth of the ulcer and from its edge by tissue growth, so that as a rule no cosmetic corrections are subsequently necessary. In this connection side effects which might be objectively expected, such as an increase in blood pressure, are absent.

Stasis dermatoses and post-thrombotic dermatitises which are characterized by scaling and frequently large-size medium-to-dark-brown spots surprisingly show a definite lightening of the color of the infected regions of the skin after only a short time following the use of dihydroergotamine in accordance with the invention. After treatment for several weeks, the color and elasticity of the skin have again adapted themselves to the normal surrounding area.

OBJECTS OF THE INVENTION

It is an object of the present invention to provide an improved method for the local or topical treatment of trophic disturbance which comprises an effective amount of dihydroergotamine or a pharmaceutically-acceptable salt thereof which is effective for the alleviation, amelioration, or cure of the said condition, and pharmaceutical compositions useful in carrying out the said method as well as a method for the preparation of the said compositions. Another object is to provide such pharmaceutical compositions in solid, semisolid, and liquid forms. Other objects of the invention will become apparent hereinafter and still others will be obvious to one skilled in the art.

SUMMARY OF THE INVENTION

In summary, what I claim as my invention, inter alia, comprises the following:

A method for the local treatment of trophic disturbances comprising the step of administering to a subject in need thereof an amount of dihydroergotamine or a pharmaceutically-acceptable salt thereof effective for alleviation, amelioration, or cure of the said condition, such method wherein the trophic disturbance is stasis dermatoses, ulcus cruris venosum, or decubital ulcers. Also, a pharmaceutical composition for topical application which contains an effective amount, between about 0.001 and 99.9% by weight, of dihydroergotamine and/or a salt thereof, and a pharmaceutically- and topically-acceptable carrier or diluent, such a liquid pharmaceutical composition characterized by the fact that it contains between about 0.01 and 5% by weight of dihydroergotamine and/or a salt thereof and between about 99.99 and 95% by weight of diluent, such a semisolid pharmaceutical composition characterized by the fact that it contains between about 0.01 and 5% by weight of dihydroergotamine and/or a salt thereof and between about 99.99 and 95% by weight of diluent, such liquid pharmaceutical composition characterized by the fact that it contains more than 10% by weight of propyleneglycol and/or glycerol or a mixture thereof, such semisolid pharmaceutical composition characterized by the fact that it contains more than 10% by weight of propylene-glycol and/or glycerol or a mixture thereof, such solid pharmaceutical composition characterized by the fact that it contains between about 0.01 and 99.99% by weight of dihydroergotamine and/or a salt thereof and between about 0.01 and 99.99% of diluent, such pharmaceutical composition containing another active ingredient, such pharmaceutical composition characterized by the fact that the pH is about 3.5 to 8.5, and such a pharmaceutical composition characterized by the fact that the dihydroergotamine or its salt is predominantly or completely dissolved and, moreover, such method wherein the dihydroergotamine is administered in the form of a prodrug thereof or in the form of a metabolite thereof, namely, 8'-hydroxydihydroergotamine or 8',10'-dihydroxydihydroergotamine, and such composition wherein the dihydroergotamine is present in the form of a prodrug or metabolite thereof, for example, 8'-hydroxydihydroergotamine or 8',10'-dihydroxydihydroergotamine.

FURTHER DETAILS OF INVENTION

The employment of dihydroergotamine or a pharmaceutically-acceptable salt thereof, such as the hydrochloride, the methanesulfonate, ethanesulfonate, tartrate, maleate, succinate, or other salt suitable for use in the local treatment of the above-indicated trophic disturbances, can be effected in the form of the selected compound per se but preferably in the form of a liquid, semisolid, or solid formulation thereof as well as a formulation which contains either a prodrug derivative thereof or therefor or an active metabolite of dihydroergotamine, for example 8'-hydroxydihydroergotamine and 8',10'-dihydroxydihydroergotamine, alone or together with dihydroergotamine.

Liquid drugs in this sense are solutions in the form of drops, tinctures and sprays, suspensions, emulsions and dispersions. Semisolid forms are, for instance, gels, ointments, creams and foams, while solid forms are, for instance, powders, granulates, pellets and microcapsules.

The forms of medication may contain, as far as possible, non-irritating diluents among which, in addition to water, use can be made of monohydric alcohols, polyhydric alcohols, polyglycols as well as glycerol formaldehyde, dimethyl isosorbide, and natural and synthetic oils and esters. Ethanol, glycerol, propanediol, polyethylene glycols, and Miglyol(TM) (mixture of saturated vegetable $C_8$–$C_{12}$ fatty acids) may be mentioned by way of example as a few typical representatives. For the preparation of semisolid forms of administration, there are suitable, in addition to the solvents mentioned above, also base compositions such as, for instance, bentonite, veegum, guar meal, and cellulose derivatives such as methyl cellulose, carboxymethyl cellulose, as well as polymers of vinyl alcohol and vinyl pyrrolidone, alginates, pectins, polyacrylates, solid and liquid polyethylene glycols, paraffins, fatty alcohols, petroleum jellies and waxes, fatty acids and fatty acid esters. Solid forms of medication contain either the active substance undiluted or with diluents such as, for instance, colloidal silica, talc, lactose, starch powders, sugars, cellulose derivatives and gelatins, metal oxides and metal salts. The forms of medication can furthermore also contain other components such as preservatives, stabilizers, surface-active agents, emulsifiers and penetration promoters, spreading agents, buffers and propellants. The diluting agents an auxiliary substances mentioned as example are not specific to the form of drug. They can be used optionally for different forms. Compositions which ensure auto-sterility based on their characteristics are particularly preferred, it being possible in this case to dispense with added preservatives. For this there are suitable compositions which contain more than 10% by weight propylene glycol and/or glycerol or mixtures thereof and which furthermore are characterized by relatively good tolerance.

The methods of preparing the liquid and semi-solid forms are preferably so selected that the active substance is present in predominantly or completely dissolved form or is uniformly distributed so as to develop its action directly.

The methods of producing the medicinal forms are known per se. However, an additional requirement for the methods is that, in particular, the liquid and semisolid forms of administration be aseptic after manufacture and filling or packing so as to prevent a secondary infection of the diseased areas to be treated. The minimum requirement is that the medicinal forms contain less than 1000 and preferably less than 100 reproductive non-pathogenic microorganisms.

The pH of liquid and semisolid forms of drug can be so adjusted and possibly corrected as to approximate the physiological conditions. In this connection, a pH range of 3.5 to 8.5, and preferably 5 to 7.8, is particularly desirable.

In addition to the foregoing, administration can also be effected by means of treated strips of gauze, bandages and plasters which are impregnated or covered with the said forms of drugs, or combinations thereof. In any event, the method of administration to a subject in need thereof generally comprises the topical administration of an effective amount for the alleviation, amelioration, or cure of trophic disturbances in the said subject.

The concentration of active substance in the drug compositions is an effective amount, which is generally between about 0.001 and 99.9% by weight, preferably about 0.01 to 5% by weight, in the liquid and semisolid forms and 0.01 to 99.9% by weight in the solid forms; i.e., the pure active substance can be used undiluted with the use of suitable dosing aids for precise dosing. The difference from 100% by weight results from the corresponding portion of diluent or the auxiliary substances used.

The medicinal forms of drugs are filled in known containers such as bottles, tubes, sprinkling or shaking cans, and sealed edge bags which are possibly equipped with dosaging aids such as droppers, dosaging valves and dosaging chambers.

DETAILED DESCRIPTION OF INVENTION

The following Examples are given to illustrate the invention, but are not to be construed as limiting.

EXAMPLE 1

A 56-year old female patient who had been suffering for 42 years from an ulcus cruris venosum at her left ankle was considered after treatment by ordinary principles of treatment, including unsuccessful skin transplants, as having fully exhausted clinical therapy.

At the start of the local treatment with dihydroergotamine, the ulcer had a size of about 10×6 cm with a depth of 0.5 to 1 cm. The wound itched, discharged, gave off a disagreeable odor and was covered with smeary, yellowish coatings. The wound was surrounded by a stasis dermatosis which was about three times as large. At the start of the treatment, the bone of the lower leg could be seen in the depth of the wound. Treatment was effected in the manner that a solution in accordance with Example 4 was first of all applied in drops to the wound. Strips of gauze soaked with the solution were then applied directly onto the wound. The solution was so dosed that about 0.01 mg of dihydroergotamine was present per square centimeter of wound surface. After only several days of local treatment of the wound the itching, discharge and disagreeable odor disappeared, followed by the formation of marginal granulation tissue, granulation islands and vascularization after several weeks.

After treatment for four months the ulcer was reduced to the size of a matchbox and a clearly covering growth of tissue from the depth could be noted. After a further three months of treatment, the wound was scarred and completely healed. The indications of stasis dermatosis had almost completely disappeared.

This success in treatment is all the more surprising since the patient in question represented the worst condition conceivable for a cure (excess weight, a standing occupation, a smoker, a history of more than ten years).

EXAMPLE 2

In a 75-year old female patient with severe cerebral sclerosis and heart disease, several ulcers were treated. One ulcer in the region of the sacrum was of a size of 7×5 cm. Smaller ulcers were present in the region of both shoulder blades and both heels. The treatment was carried out with preprepared bandages of the forms of administration in accordance with the invention, especially the solution of Example 4. The shoulder ulcers were completely cured by the end of three weeks, the sacral ulcer in five weeks, and heel ulcers in three and five and a half weeks, respectively. In each case there was complete closure of the wound.

EXAMPLE 3

A 50-year old male patient had been suffering for 12 years with intensive medium-to-dark-brown discolorations, indications of a stasis dermatitis or post-thrombotic dermatosis, particularly on the left lower leg in the tibial region.

The spotted areas of the patient were rubbed, after careful washing, with a dosage form of the type of the invention containing dihydroergotamine, especially the gel of Example 5. After only fourteen days a definite lightening of the color of the regions of the skin could be observed. After ten weeks treatment, the color and elasticity of the skin were completely normal.

The following examples indicate compositions of medicinal forms and methods for the preparation thereof which are suitable for the local treatment of trophic disturbances with dihydroergotamine.

EXAMPLE 4

Solution

| | |
|---|---|
| Dihydroergotamine methanesulfonate | 2.00 g |
| Propylene glycol | 556.60 g |
| Glycerol | 52.50 g |
| Water | 438.90 g |
| | 1,050.00 g |

Dihydroergotamine methanesulfonate is dissolved, with stirring, in the mixture of propylene glycol and glycerol. After addition of the water, the solution is subjected to sterile filtration and filled into bottles.

The solution contains 2.0 mg of active substance per ml of solution. The bottles are provided with a dropper which makes it possible to apply 0.1 mg of active substance per drop.

EXAMPLE 5

Gel

| | |
|---|---|
| Dihydroergotamine methanesulfonate | 2.00 g |
| Propylene glycol | 700.00 g |
| Bentonite (Bentone LT) | 29.00 g |
| Glycerol | 45.00 g |
| Water | 224.00 g |
| | 1,000.00 g |

Bentone LT is heat-sterilized and then suspended in one part of propylene glycol. Glycerol and water are first of all incorporated into the suspension followed by a solution of dihydroergotamine methanesulfonate in the remaining propylene glycol.

The preparation is effected at room temperature under vacuum under aseptic conditions. An easily spreadable gel having a viscosity of about 32,000 centipoise and a pH of 7.6 is obtained, which is filled into tubes having an inner protective varnishing.

EXAMPLE 6

Gel

| | |
|---|---|
| Dihydroergotamine methanesulfonate | 4.00 g |
| Propylene glycol | 500.00 g |
| Sodium carboxymethyl cellulose | 17.00 g |
| Glycerol | 45.00 g |
| Water | 433.83 g |
| Propylgallate | 0.05 g |
| Thiodipropionic acid | 0.10 g |
| Titriplex III (ethylene diamine triacetic acid) | 0.02 g |
| | 1,000.00 g |

Sodium carboxymethl cellulose is first of all suspended in one part of propylene glycol. A solution of glycerol, water, propylgallate, thiodipropionic acid, and Titriplex III is stirred into the suspension. The dihydroergotamine methanesulfonate, dissolved in the remaining amount of propylene glycol, is then added to the mixture.

The preparation is carried out at room temperature under vacuum and aseptic conditions.

An easily spreadable gel of a viscosity of about 32,000 centipoise and a pH of 6.3 is obtained. 5 g of the gel are applied, spread uniformly over a sterile multi-layer gauze having a surface of about 100 cm², covered with a cover foil and sealed in a sealed round aluminum bag.

The gauze ready for use contains 0.2 mg of active substance per square centimeter.

EXAMPLE 7

Powder

| | |
|---|---|
| Dihydroergotamine methanesulfonate | 10.0 g |
| Lactose | 188.0 g |
| Colloidal silica | 2.0 g |

Dihydroergotamine methane sulfonate and lactose are granulated wet with the use of a water/ethanol mixture. The solvent mixture is then evaporated and the coarse granulate is crushed by means of a granulator to a particle size of less than 100μ. After the silica has been added, the powder is introduced into a shaker can.

The powder can be shaken on in the amount required, the active concentration of 0.05 g per g of powder permitting a very thin application.

EXAMPLE 8

| Dihydroergotamine methane sulfonate | 10.0 g |
| Propylene glycol | 3,515.0 g |
| Hydroxyethylcellulose (Natrosol(R) 250 HX) | 60.0 g |
| Glycerol | 225.0 g |
| Water | 1,190.0 g |
| | 5,000.0 g |

2,000 g of propylene glycol are heated to 60° C. The hydroxyethyl cellulose is suspended therein with stirring. A mixture of 225 g of glycerol and the indicated amount of water are added to the suspension and stirred for one hour. Cooling is then effected to room temperature and a solution of dihydroergotamine in 1515 g of propylene glycol is introduced while stirring. The stirring is continued for one hour under vacuum.

The production is effected under sterile conditions. A readily spreadable, clear gel of a viscosity of 10,500 centipoises and a pH of 5.5 is obtained.

The gel is introduced in an amount of 30 g into aluminum tubes which have an inner protective coating.

EXAMPLE 9

In a 39-year-old female patient, a varicosis of both lower legs as well as a circular ulcer on the left lower leg of a diameter of about 1 cm and a depth of 4 mm was diagnosed. The ulcer was surrounded by a reddening of the skin of a width of 5 mm and had a smeary wound covering.

The ulcer was treated with a dihydroergotamine gel according to Example 8. The gel was applied in a thin layer to the bottom of the ulcer and to the surrounding area and covered with gauze. The bandage was replaced every day. After two days the wound was cleaned; after seven days the redness of the skin disappeared. After two months the ulcer was closed with a thin layer of skin over it.

EXAMPLE 10

A rectangular ulcus cruris was diagnosed on the left thigh of a 59-year-old female patient. The wound had an area of about 4×2.5 cm and was 3 mm deep. It was surrounded by a wide, very red, wound border. The wound niche and the bottom of the ulcer were covered with a smeary, strongly-smelling wound covering.

Dihydroergotamine gel according to Example 8 was applied to the bottom of the ulcer and to the edges of the wound in a thin layer and more thickly within the wound niches. The wound was covered with gauze. The bandage was changed every day. The wound was cleaned after three days. By the end of seven days the redness of the skin had disappeared. After five days there could be noted a clear granulation in the wound niches with a slight, light-red bleeding from the bottom of the ulcer. The wound niches were closed at the end of fourteen days. The ulcer was healed at the end of ten weeks, covered with a thin layer of new skin.

EXAMPLE 11

Varicosis of both legs, venous edema of both feet, and lymphedema of both arms and hands was diagnosed in a 62-year-old female patient. On the left thigh, just above the ankle joint, there was an ulcus cruris of a diameter of 1.5 cm and a depth of 4 mm. The surrounding skin was without indication of irritation, and the wound was relatively clean.

Dihydroergotamine gel according to Example 8 was applied in a thin layer onto the bottom of the wound and the wound covered with gauze. The bandage was changed every day. After twelve weeks the wound was closed and covered by tender new skin.

EXAMPLE 12

An 89-year-old female patient suffered from a decubital ulcer over the sacrum having an area of 3×2 cm. The bottom of the ulcer was smeary.

Dihydroergotamine gel according to Example 8 was applied in a thin layer, and the ulcer covered with gauze. The bandage was changed every day. After two days the wound was cleaned. After four weeks there was closure of the wound with a thin covering of skin.

According to the present invention, not only dihydroergotamine itself, or a pharmaceutically-acceptable salt thereof, but also a prodrug, e.g., the dimethanolate, which converts thereinto upon therapeutic administration, or a pharmacologically-active metabolite thereof which is produced by physiological interaction with tissue or tissue enzymes, such as the primary metabolite 8'-hydroxydihydroergotamine or 8',10'-dihydroxydihydroergotamine, may be employed with equal facility. However, due to its ready availability at the present moment, dihydroergotamine itself or a salt thereof is the preferred active ingredient of the topical compositions of the present invention and is the active ingredient of choice in the method of treatment according to the present invention.

EXAMPLE 13

The same results are obtained when employing a prodrug for dihydroergotamine or a salt thereof, or an active metabolite thereof, such as 8'-hydroxydihydroergotamine or 8',10'-dihydroxydihydroergotamine either alone or together with dihydroergotamine or a salt thereof.

In conclusion, from the foregoing, it is apparent that the present invention provides a novel topical or local method for the treatment of trophic disturbances, especially stasis dermatoses, ulcus cruris venosum, and decubital ulcers, involving the local or topical application of dihydroergotamine or a pharmaceutically-acceptable salt thereof, or a prodrug or metabolite thereof, as well as novel topical pharmaceutical compositions thereof containing the same together with a pharmaceutically- and topically-acceptable carrier or diluent, all having the foregoing enumerated characteristics and advantages.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope which can be legally accorded to the appended claims.

I claim:

1. A method for the local treatment of trophic disturbances of the skin involving venous insufficiency comprising the step of topically administering to a subject in need thereof a composition consisting essentially of an amount of dihydroergotamine or a pharmaceutically-acceptable salt thereof which is effective for alleviation, amelioration, or cure of the said condition.

2. The method of claim 1 wherein the trophic disturbance is stasis dermatoses.

3. The method of claim 1 wherein the trophic disturbance is ulcus cruris venosum.

4. The method of claim 1 wherein the trophic disturbance is decubital ulcers.

5. The method of claim 1, wherein the dihydroergotamine is administered in the form of a prodrug thereof, namely, dihydroergotamine dimethanolate.

6. The method of claim 1, wherein the dihydroergotamine is administered in the form of a metabolite thereof, namely, 8'-hydroxydihydroergotamine or 8',10'-dihydroxydihydroergotamine.

7. Semisolid pharmaceutical composition for topical application which consists essentially of an effective amount, between about 0.001 and 99.9% by weight, of dihydroergotamine or a salt thereof, and a pharmaceutically- and topically-acceptable carrier or diluent.

8. Semisolid pharmaceutical composition according to claim 7, characterized by the fact that it contains between about 0.01 and 5% by weight of dihydroergotamine and/or a salt thereof and between about 99.99 and 95% by weight of diluent.

9. Semisolid pharmaceutical composition according to claim 8, characterized by the fact that it contains more than 10% by weight of propyleneglycol and/or glycerol or a mixture thereof.

10. Solid pharmaceutical composition according to claim 7, characterized by the fact that it contains between about 0.01 and 99.99% by weight of dihydroergotamine and/or a salt thereof and between about 0.01 and 99.99% of diluent.

11. Pharmaceutical composition according to claim 7, characterized by the fact that the pH is about 3.5 to 8.5.

12. Pharmaceutical composition according to claim 7, characterized by the fact that the active substance dihydroergotamine or its salt is predominantly or completely dissolved.

13. The pharmaceutical composition of claim 7, wherein the dihydroergotamine is present in the form of a prodrug thereof, namely, dihydroergotamine dimethanolate.

14. The pharmaceutical composition of claim 7, wherein the dihydroergotamine is present in the form of a metabolite thereof, namely, 8'-hydroxydihydroergotamine or 8',10'-dihydroxydihydroergotamine.

15. Pharmaceutical composition of claim 7, wherein the composition is in the form of a spreadable topical gel.

16. Pharmaceutical composition of claim 7, wherein the composition is in the form of a propylene glycol- or glycerol-containing topical gel.

17. Pharmaceutical composition of claim 7, wherein the composition is in the form of a spreadable gel, and wherein the amount of propylene glycol and/or glycerol therein is greater than about 10% and up to about 75% by weight.

18. Pharmaceutical composition of claim 7, wherein the composition is in the form of a spreadable topical gel, and wherein the amount of propylene glycol and/or glycerol therein is between about 50% and about 75% by weight.

* * * * *

UNITED STATES PATENT AND TRADEMARK OFFICE
CERTIFICATE OF CORRECTION

PATENT NO. : 4,916,132

DATED : Apr. 10, 1990

INVENTOR(S) : Hubert Seibel

It is certified that error appears in the above-identified patent and that said Letters Patent is hereby corrected as shown below:

Title page, [56], References Cited, Other Publications. line 1: "Nauarro" should read -- Navarro --.

Column 1, line 25; "decutibal" should read -- decubital --.
Column 1, line 57; "insufficiency as" should read -- insufficiency, as --
Column 1, line 58; "prophylaxis is" should read -- prophylaxis, is --.
Column 2, line 36; "method as" should read -- method, as --.
Column 3, line 30; "se but" should read -- se, but --.
Column 3, line 31; "thereof as" should read -- thereof, as --.
Column 3, line 33; "therefor, or" should read -- therefor, or --.
Column 3, line 46; "polyglycols as" should read -- polyglycols, as --.
Column 3, line 56; "cellulose, carboxymethyl" should read -- cellulose or carboxymethyl --.
Column 4, line 1; "an" should read -- and --.
Column 8, line 50; "-dihydroxydihydroergotamine either" should read ---dihydroxydihydroergotamine, either --.
Column 9, line 7; "insufficienty" should read -- insufficiency -- .

UNITED STATES PATENT AND TRADEMARK OFFICE
CERTIFICATE OF CORRECTION

PATENT NO. : 4,916,132

DATED : Apr. 10, 1990

INVENTOR(S) : Hubert Seibel

It is certified that error appears in the above-identified patent and that said Letters Patent is hereby corrected as shown below:

Column 10, line 3; "10. Solid" should read
-- 10. Semisolid --.

Signed and Sealed this

Twentieth Day of August, 1991

Attest:

HARRY F. MANBECK, JR.

Attesting Officer

Commissioner of Patents and Trademarks